United States Patent [19]

Bzdula

[11] Patent Number: 4,498,305
[45] Date of Patent: Feb. 12, 1985

[54] PROBE FOR MEASURING ELECTRICAL CONDUCTANCE

[75] Inventor: Joseph A. Bzdula, Fulton, N.Y.

[73] Assignee: Carrier Corporation, Syracuse, N.Y.

[21] Appl. No.: 547,313

[22] Filed: Oct. 31, 1983

Related U.S. Application Data

[62] Division of Ser. No. 353,768, Mar. 1, 1982, Pat. No. 4,449,396.

[51] Int. Cl.$^3$ .................. F25B 43/02; G01K 13/00
[52] U.S. Cl. .................................. 62/84; 62/129
[58] Field of Search .............. 62/84, 85, 125, 126, 62/127, 129, 192, 193, 195, 468, 469, 474, 475; 200/61.04; 340/602; 73/336.5; 338/34; 73/61.1 R

[56] References Cited

U.S. PATENT DOCUMENTS

| | | | |
|---|---|---|---|
| 2,863,299 | 12/1958 | Ammons | 62/129 X |
| 3,288,960 | 11/1966 | Miller | 200/61.04 X |
| 3,671,912 | 6/1972 | La Sota | 200/61.04 X |
| 3,846,730 | 11/1974 | Hamilton | 62/129 X |
| 3,959,980 | 6/1976 | Hamilton | 62/126 |
| 4,090,371 | 5/1978 | Keane | 62/129 |

Primary Examiner—Harry B. Tanner
Attorney, Agent, or Firm—Douglas L. Miller

[57] ABSTRACT

A probe for measuring electrical conductance to determine water concentration in a fluid is disclosed. The probe comprises a pair of spaced apart electrodes and a bridge of protein gel between the electrodes. The probe is especially useful for monitoring water concentration in the lubrication oil for a compressor drive train of a hermetic vapor compression refrigeration system. In such a refrigeration system the water concentration in the lubrication oil corresponds to water concentration in the refrigerant of the refrigeration system.

1 Claim, 2 Drawing Figures

PROBE FOR MEASURING ELECTRICAL CONDUCTANCE

This application is a division of application Ser. No. 353,768, filed Mar. 1, 1982, now U.S. Pat. No. 4,449,396.

BACKGROUND OF THE INVENTION

The present invention relates to probes for measuring electrical conductance and more particularly relates to probes for determing water concentrations in fluids. Also, the present invention relates to methods of determining water concentration in the refrigerant of a hermetic vapor compression refrigeration system.

Water concentration measurements are commonly needed for a variety of purposes. For example, when operating a hermetic vapor compression refrigeration system it is desirable to detect water concentration in the refrigerant of the refrigeration system. A relatively high water concentration in the refrigerant may indicate a problem such as a water leak in a heat exchanger tube. In certain situations it is desirable to detect and correct such a problem as soon as possible. Also, relative humidity sensors are often used in controls for equipment such as air conditioning and refrigeration machines.

It is especially desirable to measure water concentration in a fluid such as a lubrication oil for a compressor drive train of a hermetic vapor compression refrigeration system.

This is true because typically such a hermetic vapor compression refrigeration system has an oil lubrication system for the compressor drive train wherein refrigerant from the refrigeration system is constantly in contact with the oil of the lubrication system. Typically, in such a refrigeration system, an oil reservoir for the lubrication system is located in the compressor transmission drive housing which is vented to the suction side of the compressor to reduce windage losses in the housing. Refrigerant is continuously circulating through the compressor drive housing from the refrigeration system and there is constant contact between the refrigerant and the oil. Water and other contaminants in the refrigerant are deposited in the compressor drive lubrication oil because of the contact between the refrigerant and the oil. Since the portion of refrigerant in contact with the oil is constantly changing, the amount of contaminants in the oil tends to be an average of the contaminants in the refrigerant of the refrigeration system. Thus, the amount of a particular contaminant, such as water, in the compressor drive lubricating oil is a good indication of the amount of that particular contaminant in the refrigerant of the refrigeration system.

Testing for the water concentration in the compressor drive lubricating oil is better than directly measuring water concentration in the refrigerant because it is difficult to accurately measure water concentration in the refrigerant. In a refrigeration system, refrigerant is continually changing phase and moving through the system so that the water content of the refrigerant is not constant at all locations within the system. Also, since excess water floats on top of liquid refrigerant at various places within the system, any sample of refrigerant taken from a location, other than where the excess water is present, gives an indication of water content which is lower than the actual water concentration in the refrigeration system. Thus, choosing a sampling location is of critical importance when testing directly for water in refrigerant and in practice no sampling location provides a representative sample of the refrigerant at all times. Therefore, it is particularly desirable to test the compressor drive lubricating oil for the presence of water to determine the water concentration in the refrigeration system since the oil is not subject to random water concentration variations of the type to which the refrigerant is subjected.

Tests are known for determining water concentration in compressor drive lubricating oil wherein samples of the oil are taken and chemically analyzed. However, taking samples of the oil is relatively time consuming, costly and complex. Also, a person of training is required to conduct the chemical analysis and a sample of the oil must be taken each time it is desired to make a water concentration determination. A probe for continuously and directly measuring water concentration in oil is a preferable means of making such water concentration determinations rather than conducting a chemical analysis.

Also, it should be noted that probes are known for testing a refrigerant or air to determine its water concentration. For example, a moisture sensitive indicator which changes color upon contact with water, or an electrode made of a water absorbing salt, may be used to test for water in the refrigerant of a refrigeration system. Also, ceramic sensors are known for measuring relative humidity. One such relative humidity sensor has a water sensitive probe comprising a block of porous material formed from a spinnel chrome-zinc oxide compound which is sintered with alkaline metal at high temperatures. Porous electrodes welded to lead wires are mounted on opposite sides of the porous material. Relative humidity is measured by water molecules being absorbed and released by the crystal surface of the sintered substance and by the ceramic element, whose electrical resistance varies exponentially with relative humidity. However, these probes are not suitable for determining water concentration in oil.

SUMMARY OF THE INVENTON

Therefore, an object of the present invention is to simply and reliably determine water concentration in a fluid, especially a fluid such as oil.

Another object of the present invention is to continuously monitor water concentration in a fluid, especially a fluid such as oil.

A further object of the present invention is to simply, reliably and continuously monitor water concentration in the refrigerant of a hermetic vapor compression refrigeration system.

These and other objects of the present invention are attained by a probe comprising a pair of spaced apart electrodes and a bridge of protein gel between the electrodes. The resistance between the electrodes varies in proportion to the amount of water absorbed by the protein gel. The amount of water absorbed by the protein gel is proportional to the water concentration in the surrounding fluid. When used in a circulating fluid it is preferable that the protein gel comprise gelatin and a water permeable substance such as cellulose acetate. The gelatin absorbs water in proportion to the water concentration in the surrounding fluid and the cellulose acetate gives the probe rigidity while maintaining water sensitivity since the acetate is water permeable.

Further, according to the present invention, a probe as described above may be used to monitor water concentration in the refrigerant of a hermetic vapor compression refrigeration system by placing the probe in the lubrication oil for the compressor drive train of the refrigeration system. One convenient location for the probe is in an oil reservoir in the compressor transmission drive housing. After placing the probe in the oil, the conductance of the probe is measured during a selected time period of operation of the refrigeration system to establish a baseline (reference) level of conductance measurements. Then, the conductance of the probe is measured during regular operation of the refrigeration system and these conductance measurements are compared to the baseline level conductance measurements to monitor changes in water concentration in the oil. The water concentration in the oil corresponds to water concentration in the refrigerant of the refrigeration system. Thus, by continuously monitoring the conductance of the probe it is possible to continuously monitor the water concentration in the refrigerant of the refrigeration system.

BRIEF DESCRIPTION OF THE DRAWING

Other objects and advantages of the present invention will be apparent from the following detailed description in conjunction with the accompanying drawing in which.

DESCRIPTION OF THE PREFERRED EMBODIMENTS

Figure 1:
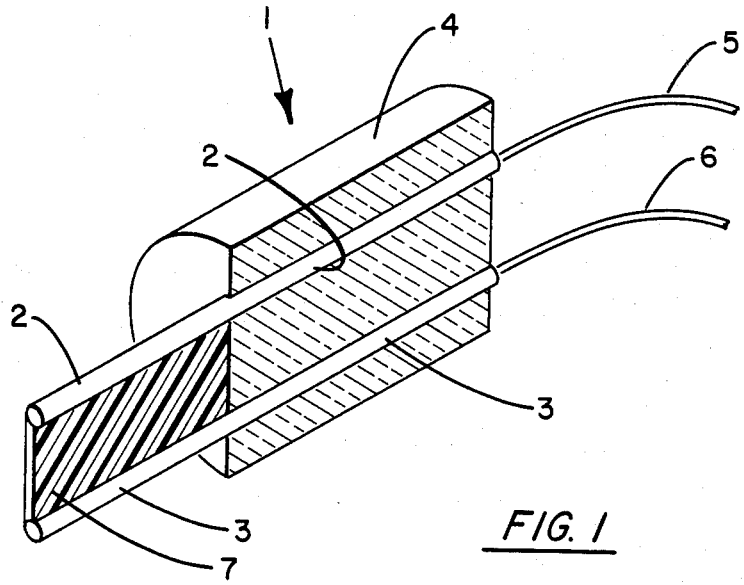
FIG. 1 is a cross-sectional view of a probe for measuring electrical conductance according to the principles of the present invention.

Referring to FIG. 1, a cross-sectional view of a probe 1 for measuring electrical conductance according to the principles of the present invention is illustrated. The probe 1 comprises a pair of spaced apart electrodes 2 and 3 with each electrode having a top part embedded in a probe body 4 made of a non-conducting material such as polyvinylchloride (PVC). The bottom part of each electrode 2 and 3 extends out from the probe body 4. The electrodes 2 and 3, which may be copper wires, are connected by electrical connectors 5 and 6, respectively, to electronics (not shown) for measuring resistance between the electrodes 2 and 3. Conductivity of the probe 1 is determined from the measured resistance and conductance is calculated from the conductivity. Alternatively, a conductance meter, such as a Yellow Springs Instrument (YSI) Model 32, may be connected to the electrical connectors 5 and 6 to directly measure conductance of the probe 1.

As shown in FIG. 1, a protein gel forms a potentially conductive bridge 7 between the electrodes 2 and 3 of the probe 1. One way of making the bridge 7 is to dip the electrodes 2 and 3 in a water solution of protein gel. Then, the electrodes 2 and 3 are removed from the solution and rotated in air so that the water evaporates while the gel, picked up by the electrodes 2 and 3, is allowed to dry and harden between the electrodes 2 and 3.

The protein gel may be any of a large number of substances whose conductivity depends on the amount of water absorbed by the substance and which when placed in a fluid absorbs and releases water in proportion to the water concentration in the surrounding fluid. One such protein gel is gelatin made by boiling a collagen in water. The exact chemical composition of the gelatin may vary depending on the composition of the particular collagen from which the gelatin is extracted but, basically, the gelatin is a mixture of polypeptides having varying percentages of amino acids. Percentages of amino acids in a typical gelatin are approximately 35% glycine, 11% alanine, 12% proline, and 9% hydroxyproline.

The protein gel may be composed of a substance other than substantially pure gelatin. For example, the protein gel may comprise gelatin and a water permeable substance, such as cellulose acetate. The water permeable substance provides support for the gelatin to prevent erosion of the gelatin from between the electrodes 2 and 3 of the probe 1 by fluid circulating around the probe 1. If desired, other substances for providing support to the gelatin may be present in the protein gel in lieu of or in addition to a water permeable substance such as cellulose acetate. However, the overall percentages in the protein gel of such other substances should be kept relatively low if water sensitivity of the gel is to be maintained at a relatively high level.

Figure 2:
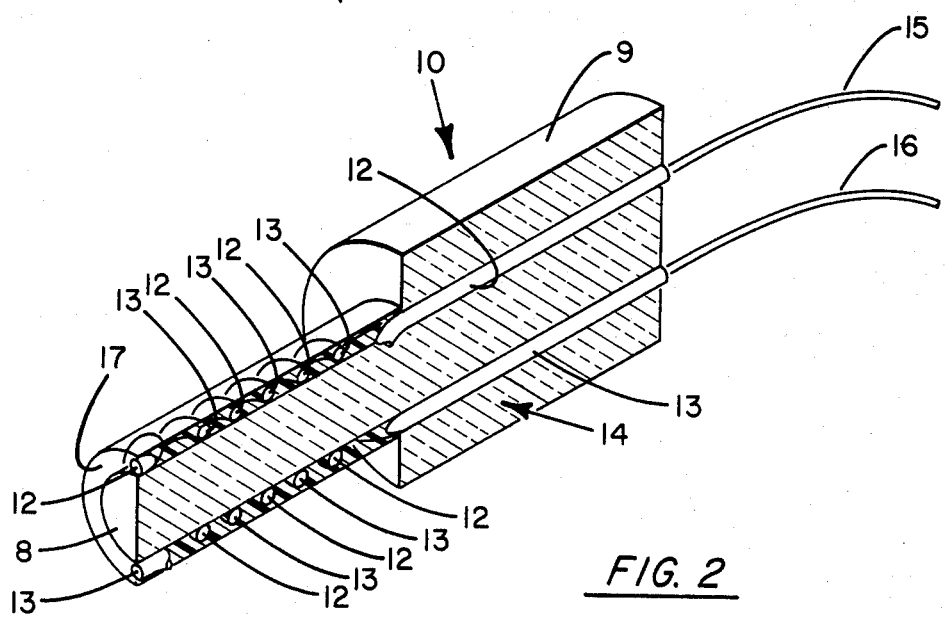
FIG. 2 is a cross-sectional view of an alternative embodiment of a probe for measuring electrical conductance according to the principles of the present invention. This probe embodiment is especially designed for use in an oil reservoir in a compressor transmission drive housing of a hermetic vapor compression refrigeration system to monitor water concentration in the oil.

Referring to FIG. 2, a cross-sectional view of another embodiment of a probe 10 for measuring electrical conductance according to the principles of the present invention is shown. The probe 10 includes a pair of spaced apart electrodes 12 and 13 and a probe body 14 having a generally cylindrical bottom portion 8 and a top portion 9. Each of the electrodes 12 and 13 has a top part embedded in the top portion 9 of the probe body 14 and a bottom part extending out from the top portion 9. The bottom parts of the electrodes 12 and 13 are helically wound on the outer surface of the bottom portion 8 of the probe body 14. Electrical connectors 15 and 16 for connecting the electrodes 12 and 13, respectively, to electronics, such as a conductance meter (not shown), are attached to the top parts of the electrodes 12 and 13. A bridge 17 of protein gel covers the electrodes 12 and 13 to form a potentially conductive coating over the electrodes 12 and 13.

As shown in FIG. 2, a typical probe 10 may be constructed by using insulated copper wires for the electrodes 12 and 13. The insulation on the outer surfaces of the bottom parts of the wires is abraded off after the wires are helically wound on the bottom portion 8 of the probe body 14. This leaves insulation between each turn of wire to prevent a short circuit condition and exposes a portion of each wire for conduction. The protein gel forms a coating or bridge 17 over the exposed outer surfaces of the wires. The probe body 14 may be made of a non-conducting material such as polyvinylchloride (PVC).

There may be a large number of turns of wire on the bottom portion 8 of the probe body 14 depending on the amount of surface area which it is desired to coat with protein gel. The sensitivity and reliability of the probe 10 are enhanced if this surface area is relatively large. The thickness of the protein gel determines the response time of the probe 10 to variations in water concentration in the surrounding fluid. Thinner coatings decrease the response time of the probe 10.

In operation, a probe constructed as shown in either FIGS. 1 or 2, is placed in a fluid to monitor water concentration in the fluid. For example, the probe may be placed in air to operate as a relative humidity sensor or in an oil reservoir in a compressor transmission drive housing of a hermetic vapor compression refrigeration system to measure water concentration in the oil. Electronics for measuring conductance of the probe 1 is connected to the probe through the electrical connectors (15 and 16 or 5 and 6). If desired the probe may be calibrated by measuring the conductance of the probe during a time period when water concentration in the surrounding fluid is known. This conductance data may be used as a baseline (reference) for comparison purposes when determining water concentrations in the surrounding fluid with the probe. Alternatively, the probe may be used to monitor changes in water concentration in the surrounding fluid.

A probe 10 having a helical electrode configuration on a supporting member 8, as shown in FIG. 2, is especially suitable for preventing significant erosion of the protein gel coating 17 in a circulating fluid environment. Therefore, this type of probe 10 is especially suitable when the probe 10 is used in an oil reservoir in a compressor transmission drive housing of a hermetic vapor compression refrigeration system to monitor water concentration in the oil. Electronics, such as a conductance meter, for measuring conductance of the probe 10 may be located outside of the compressor transmission drive housing. The conductance meter is electrically connected to the electrodes 12 and 13 of the probe 10 via the electrical connectors 15 and 16 which extend through and outside of the compressor housing. Changes in water concentration in the lubrication oil result in changes in conductivity of the probe 10 resulting in changes in conductance measured by the meter. An increase in water concentration in the oil increases the amount of water absorbed by the protein gel coating 17 on the probe 10 thereby increasing the conductivity of the probe 10. A decrease in water concentration in the oil causes the protein gel coating 17 to release water to the oil thereby decreasing the conductivity of the probe 10. These changes in conductivity are detected as changes in readings of the conductance meter.

As discussed previously, because of the continuous, circulating contact between the refrigerant from the refrigeration system and the oil in the oil reservoir, the water concentration in the oil is an indication of the water concentration in the refrigerant. An unusually high water concentration in the refrigerant may, in turn, indicate a problem such as a water leak in a heat exchanger tube. If the monitored water concentration in the oil is abnormal then steps can be taken to determine the cause of the abnormal reading and corrective action taken, if necessary.

Also, it should be noted that contaminants, such as chlorides, in the refrigeration system may be dissolved in the water absorbed by the protein gel coating 17 of the probe 10 and that the absolute values of the conductance readings may depend on the amount of such contaminants present in this water. Thus, the probe 10 may be used to detect the presence of such contaminants if the probe 10 is calibrated so that the absolute conductance readings are indicative of the presence of such contaminants. Of course, the relative conductance readings of the probe 10 will always be directly proportional to the amount of water absorbed by the protein gel.

Conductive probes 10 built as shown in FIG. 2 have been tested by monitoring conductance of the probes when placed in a vessel containing an oil and water mixture which varied in water concentration. The following are three examples of these tests.

TEST I, 100% GELATIN

A mixture of gelatin in water was slowly heated to 150° F. and stirred to form a colloidal gelatin solution having 10% gelatin by weight. A probe 10, designed as shown in FIG. 2 having polyvinylchloride (PVC) as the nonconductors 8 and 9, and having twenty-eight gauge insulated copper wire with abraded outer surfaces, as electrodes 12 and 13, helically wound on the nonconductor 8, was dipped into the colloidal gelatin solution so that only the electrodes 12 and 13 of the probe 10 entered the solution. The probe 10 was removed from the solution and excess solution material was allowed to drain off of the electrodes 12 and 13. Then, the probe was rotated in air to evenly coat the electrodes 12 and 13 while evaporating substantially all of the water thereby leaving an approximately 100% gelatin coating 17. When the coating 17 was found to no longer flow, it was allowed to dry four hours at 70° F. and a conductance reading of five micromhos was found. The coated probe 10 was placed in the vessel containing the oil mixture whose water concentration varied and the conductance of the probe 10 was monitored. The conductance of the probe 10 was found to be directly proportional to the water concentration in the oil. However, the 100% gelatin coating 17 was found to be subject to erosion when exposed to circulating oil having in excess of 100 parts per million water.

TEST II, 95% GELATIN/5% CELLULOSE ACETATE

A first mixture of 10% cellulose acetate with acetic acid and a second mixture of 10% gelatin with acetic acid were prepared by mixing and heating to 150° F. A gelatin-cellulose acetate mixture having 5% by weight cellulose acetate was obtained by mixing 10 grams of the first mixture with 190 grams of the second mixture. This cellulose acetate-gelatin-acetic acid mixture was applied to the abraded electrodes 12 and 13 of a probe 10, as discussed with respect to Test I, by dipping the electrodes 12 and 13 into the mixture, removing the probe 10 from the mixture, and allowing the excess solution material to drain off of the probe 10. The conductive bridge (coating) 17 of protein gel between the electrodes 12 and 13 was formed by slowly heating the probe 10 over a hot plate in a ventilating hood and rotating the probe 10 to form a uniform coating 17 of the protein gel on the outside surface of the electrodes 12 and 13. The evaporation rate of the acetic acid was controlled to prevent blistering and cracking of the protein gel as the coating 17 was formed. The coated probe 10 was placed in the vessel containing the oil mixture whose water concentration varied while the conductance of the probe was monitored. Good results were achieved since the conductance of the probe 10 was proportional to water concentration in the oil and no erosion of the protein gel was observed when less than 500 parts per million water were present in the oil. However, during an extended test period of four weeks, there was some erosion of the protein gel when the water concentration in the oil exceeded 1000 parts per million.

TEST III, 92.5% GELATIN/7.5% CELLULOSE ACETATE

A mixture containing 92.5% gelatin and 7.5% cellulose acetate was prepared and a probe 10 was coated in the same manner as described with respect to test II. The coated probe 10 was placed in the vessel containing the oil mixture whose water concentration varied while the conductance of the probe 10 was monitored. Excellent results were achieved since the conductance of the probe 10 was proportional to water concentration in the oil and in the presence of up to 1500 parts per million water in oil, over a six week test period, there was no evidence of significant erosion.

Based on these test results it appears that a probe 10, constructed as shown in FIG. 2, with a protein gel having at least 5% by weight of a water permeable substance, such as cellulose acetate, prevents appreciable erosion of the gel from between the electrodes 12 and 13 in a circulating oil environment for a significant time period. Of course, the percentage of water permeable substance may vary if a substance other than cellulose acetate is used as the supporting material for the gelatin forming the protein gel.

Although the preceding discussion is primarily directed to a specific probe construction and to a probe 10 for monitoring water concentration in compressor drive train lubrication oil, it will be apparent to those of ordinary skill in the art that other probe constructions are possible and that such a probe may be used to measure water concentrations in many different fluids. For example, such a probe may be useful for directly measuring water concentrations in air or in a refrigerant. Therefore, while the present invention has been described in conjunction with particular embodiments it is to be understood that various modifications and other embodiments of the present invention may be made without departing from the scope of the invention as described herein and as claimed in the appended claims.

What is claimed is:

1. A method of monitoring water concentration in the refrigerant of a hermetic vapor compression refrigeration system having an oil lubricated compressor drive train, which comprises:

placing a probe for measuring electrical conductance in the lubrication oil for the compressor drive train;

measuring the conductance of the probe during a selected time period of operation of the refrigeration system to determine a reference level of conductance for the probe;

measuring the conductance of the probe during regular operation of the refrigeration system; and comparing the conductance measured during regular operation of the refrigeration system to the reference level of conductance to determine the change in water concentration in the oil corresponding to the change in water concentration in the refrigerant of the refrigeration system.

* * * * *